US010469777B2

(12) United States Patent
Pawlowicz et al.

(10) Patent No.: US 10,469,777 B2
(45) Date of Patent: Nov. 5, 2019

(54) METHODS, SYSTEMS AND DEVICES RELATING TO DISTORTION CORRECTION IN IMAGING DEVICES

(71) Applicant: TechInsights Inc., Ottawa, Ontario (CA)

(72) Inventors: Christopher Pawlowicz, Ottawa (CA); Alexander Sorkin, Nepean (CA); Vladimir Martincevic, Kanata (CA)

(73) Assignee: TECHINSIGHTS INC., Ottawa, Ontario (CA)

( * ) Notice: Subject to any disclaimer, the term of this patent is extended or adjusted under 35 U.S.C. 154(b) by 15 days.

(21) Appl. No.: 15/560,935

(22) PCT Filed: Mar. 22, 2016

(86) PCT No.: PCT/CA2016/050328
§ 371 (c)(1),
(2) Date: Sep. 22, 2017

(87) PCT Pub. No.: WO2016/149817
PCT Pub. Date: Sep. 29, 2016

(65) Prior Publication Data
US 2018/0054575 A1     Feb. 22, 2018

Related U.S. Application Data

(60) Provisional application No. 62/137,078, filed on Mar. 23, 2015.

(51) Int. Cl.
*H01J 37/304*      (2006.01)
*H01J 37/26*       (2006.01)
(Continued)

(52) U.S. Cl.
CPC .......... *H04N 5/357* (2013.01); *G01N 23/2251* (2013.01); *H01J 37/222* (2013.01);
(Continued)

(58) Field of Classification Search
CPC .......... H01J 37/26; H01J 37/28; H01J 37/222; H01J 37/3045; G01N 23/2251; G01N 2223/418; H04N 5/357
See application file for complete search history.

(56) References Cited

U.S. PATENT DOCUMENTS

| 5,054,097 A | 10/1991 | Flinois et al. |
| 6,236,746 B1 | 5/2001 | Chamberlain et al. |

(Continued)

FOREIGN PATENT DOCUMENTS

| EP | 0 370 322 A2 | 5/1990 |
| EP | 1 455 378 A1 | 9/2004 |

(Continued)

OTHER PUBLICATIONS

International Search Report for International Application No. PCT/CA2016/050328 dated Jun. 23, 2016 in 7 pages.

(Continued)

*Primary Examiner* — Ngoc Yen T Vu
(74) *Attorney, Agent, or Firm* — Knobbe, Martens, Olson & Bear, LLP

(57) ABSTRACT

Devices, systems and methods relating to a distortion-correcting imaging for collecting image-related data of a substrate are disclosed, comprising: a beam emitter for directing an emission at an intended location on the substrate, and a signal detector for determining a signal intensity value associated with the emission; wherein the signal intensity value is associated with a corrected substrate location, said corrected substrate location determined from the intended substrate location and a correction factor, said correction factor being a function of said intended substrate location.

19 Claims, 10 Drawing Sheets

(51) Int. Cl.
  *H01J 37/22* (2006.01)
  *H04N 5/357* (2011.01)
  *G01N 23/2251* (2018.01)
  *H01J 37/28* (2006.01)

(52) U.S. Cl.
  CPC .............. *H01J 37/26* (2013.01); *H01J 37/28* (2013.01); *H01J 37/3045* (2013.01); *G01N 2223/418* (2013.01)

(56) References Cited

U.S. PATENT DOCUMENTS

| | | | |
|---|---|---|---|
| 6,614,923 B1 | 9/2003 | Shishido et al. | |
| 7,750,296 B2 * | 7/2010 | Hitomi | H01J 37/265 250/306 |
| 8,023,723 B2 * | 9/2011 | Ito | G03F 1/86 382/144 |
| 8,119,960 B2 * | 2/2012 | Fukuyama | B82Y 20/00 250/201.3 |
| 8,253,118 B2 | 8/2012 | Zhang et al. | |
| 8,326,011 B2 | 12/2012 | Star-Lack et al. | |
| 8,407,629 B2 * | 3/2013 | Itoh | G03F 1/86 355/67 |
| 8,497,476 B2 | 7/2013 | Hatakeyama et al. | |
| 8,873,830 B2 * | 10/2014 | Yamanaka | G03F 1/86 382/144 |
| 2003/0003600 A1 * | 1/2003 | Ogura | G01N 33/525 436/518 |
| 2003/0111602 A1 | 6/2003 | Sato et al. | |
| 2004/0086170 A1 | 5/2004 | Shishido et al. | |
| 2005/0146714 A1 | 7/2005 | Kitamura et al. | |
| 2005/0265592 A1 | 12/2005 | Asano et al. | |
| 2006/0269117 A1 | 11/2006 | Seitz et al. | |
| 2008/0093551 A1 | 4/2008 | Tsuneta et al. | |
| 2008/0210867 A1 | 9/2008 | Hitomi et al. | |
| 2008/0217535 A1 | 9/2008 | Sato et al. | |
| 2009/0091727 A1 | 4/2009 | Kwan | |
| 2014/0226003 A1 | 8/2014 | Phaneuf et al. | |
| 2017/0140897 A1 | 5/2017 | Phaneuf et al. | |
| 2018/0053627 A1 | 2/2018 | Phaneuf et al. | |

FOREIGN PATENT DOCUMENTS

| | | |
|---|---|---|
| EP | 2 416 342 A2 | 2/2012 |
| WO | WO 2007/024221 A1 | 3/2007 |
| WO | WO 2015/189174 A2 | 12/2015 |

OTHER PUBLICATIONS

Written Opinion for International Application No. PCT/CA2016/050328 dated Jun. 23, 2016 in 11 pages.
Extended European Search Report in European Application No. 16767584.2 dated Nov. 27, 2018 in 11 pages.

* cited by examiner

METHODS, SYSTEMS AND DEVICES RELATING TO DISTORTION CORRECTION IN IMAGING DEVICES

FIELD OF THE DISCLOSURE

The present disclosure relates to scanning imaging systems and devices, and in particular, to methods, systems and devices relating to distortion correction of scanned images.

BACKGROUND

Scanning Imaging Devices provide an exemplary indication of image distortion problems, and they cover a broad range of systems that all could have similar problems. Such problems may result in image distortion resulting from error introduction relating to a difference between a desired location of image capture and an actual location during scanning. A number of scanning and non-scanning imaging devices may be affected and can include Electron Beam systems, Focused Ion Beam systems, Laser Imaging systems, scanning electron microscopes (SEM), transmission electron microscopes (TEM), and optical systems. Scanning systems are characterized in that the image capture mechanism is scanned over the target substrate and image data collection is collected during such scan. Non-scanning systems may make one or more image data collections of a substrate. In either case, a discrepancy between the desired location of image data collection and the actual location may result in distortion in the resulting image.

When a signal indicative of characteristics of a portion of substrate to be imaged, e.g. a surface or a cross-section of a substrate, is collected, there is often a small degree of error introduced between the actual location being analyzed on the substrate with the intended location being analyzed. The location of analysis on the substrate is related to at least the current relative position and/or relative orientation of one or all of the beam emitter, the emitted beam, the signal detector, and the substrate. The actual location of analysis may often be different from the intended location for analysis, which causes distortion when assessing characteristics of the surface or cross section, including for example when the applicable signal analysis values are assembled together to form an image. The difference between actual and intended locations may be introduced from a complex variety of sources, and interaction thereof, relating to the imaging device.

There are a variety of sources of error which may contribute to differences between the intended and actual location on the substrate for analysis. These errors may be introduced by such factors as unexpected electromagnetic field values, mechanical and control system imperfections, lens imperfections, environmental changes, scanning rates (in the case of a scanning imaging device), among myriad other factors, as well as the interactions therebetween. These and other factors introduce an offset between the intended and actual locations for data collection on the substrate being imaged, where such presumed location may be based on a number of factors, including the relative location and position of the beam emitter, the beam, the signal detector, and the substrate itself. Due to the number of sources of error, the interaction therebetween, and the complexity of accounting for all such errors in determining the actual location of sample measurement in different measurements at different times, accounting for such errors in generating an image has been difficult in all circumstances, particularly at higher resolutions and/or for larger regions. Moreover, when mosaicking such images to form a larger image, or aligning such images, mosaicked or otherwise, vertically (e.g. 3-D models), the image distortion can introduce additional uncertainties.

Another source of error for scanning image data collectors may result from differences in the relative size of the substrate capture region to the corresponding image region, as well as inconsistencies of such differences over the substrate. This may result in, for example, changes in the rate of travel of the scanning infrastructure relative to the sampling rate. As such, a sample acquired at a first location may correspond to a particular area of the surface or cross-section, which may then be used for generating image data corresponding to a pixel at that location, but due to differences in the aforementioned error at different locations on the substrate, the area at another location may be different.

This background information is provided to reveal information believed by the applicant to be of possible relevance. No admission is necessarily intended, nor should be construed, that any of the preceding information constitutes prior art.

SUMMARY

The following presents a simplified summary of the general inventive concept(s) described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

In accordance with one aspect of the present disclosure, there are provided methods, systems and devices relating to distortion correction in imaging devices that overcome some of the drawbacks of known techniques, or at least, provide a useful alternative thereto. For example, in some embodiments, improvements in accounting for complex errors in acquiring image data from a substrate are provided. For example, some embodiments provide improvements in accounting for such complexities as resolutions in images increase, and/or imaged surfaces increase relative to such resolutions.

In one embodiment, there is provided a imaging device for imaging a substrate, the device comprising a beam emitter for directing an emission at the substrate so to produce a detectable signal representative of the substrate at an intended location on the substrate; and a signal detector for detecting an intensity of said detectable signal; wherein the imaging device automatically associates said intensity with a corrected substrate location for use in generating a distortion-corrected image, wherein said corrected substrate location is determined from said intended location and a correction factor that is a function of said intended location.

In another embodiment, there is provided a distortion-correcting imaging device for collecting image-related data of a substrate, the device comprising a beam emitter for directing an emission at an intended location on the substrate, and a signal detector for determining a signal intensity value associated with the emission, wherein the signal intensity value is associated with a corrected substrate location, said corrected substrate location determined from the intended substrate location and a correction factor, said correction factor being a function of said intended substrate location.

In another embodiment, there is provided a method of correcting image distortion in an imaging device, the imaging device comprising a beam emitter for directing an emission at a substrate so to produce a detectable signal representative of the substrate at an intended location and a signal detector for determining an intensity value of said detectable signal, the method comprising the steps: causing the emission to impinge the substrate; measuring the intensity of the detectable signal associated with the intended location; determining a corrected substrate location associated with the intensity for use in generating a distortion-corrected image, the corrected substrate location determined from the intended location and a correction factor that is a function of said intended substrate location.

In another embodiment, there is provided a method of determining location-based correction information for an imaging device, the imaging device comprising a beam emitter for directing an emission at a substrate so to produce a detectable signal representative of the substrate at an intended location on the substrate, and a signal detector for determining intensity associated with said detectable signal, the method comprising the steps: placing a substrate having known surface features in the imaging device; measuring a surface feature characteristic indicative of said surface features by detecting the intensity of said detectable signal for each of a plurality of intended substrate locations while maintaining constant at least one operating characteristic of the imaging device, the signal intensity values respectively indicative of said surface feature characteristics; and determining, based on respective differences between each of a plurality measured locations of said surface features and corresponding actual locations of said surface features, an association between each measured location and corresponding actual location as a function of said measured substrate location.

In another embodiment, there is provided a method of generating an image of a substrate from an imaging device, the imaging device comprising an a beam source for directing an emission at an intended location on a substrate and a signal detector for determining a signal intensity value associated with the emission, the method comprising the steps: collecting a plurality of signal intensity values by the signal detector, each signal intensity value indicative of a substrate characteristic at an actual location; determining, for each of the plurality of signal intensity values, the actual location associated with the signal intensity value by correcting said intended substrate location using a correction factor, said correction factor being a function of said intended substrate location; and generating image pixel values for the image, each image pixel value based on respective proportions of at least one signal intensity value whose corrected substrate location corresponds to a portion of the image pixel.

In another embodiment, there is provided an imaging device for imaging a substrate, the device comprising: a beam emitter for directing an emission at the substrate so to produce a detectable signal representative of an intended area of the substrate; a signal detector for detecting a respective intensity of said detectable signal for each said intended area; and a digital processor operable to process said respective intensity to automatically associate therewith a corrected area for use in generating a distortion-corrected image, wherein each said corrected area is determined from said intended area and a correction factor associated with said intended area.

In another embodiment, there is provided a method of correcting image distortion in an imaging device, the imaging device comprising a beam emitter for directing an emission at the substrate so to produce a detectable signal representative of an intended area of the substrate, and a signal detector for detecting a respective intensity of said detectable signal for each said intended area, the method comprising: causing the emission to impinge the substrate; measuring the respective intensity associated with the intended area; for each intended area, defining a corrected area from said intended area and a designated correction factor associated with said intended area; associating said measured intensity with said corrected area; and generating a distortion-corrected image based on said associating of said measured intensity with said corrected area.

Many systems, including beam-oriented systems, generally include compensation electronics to adjust for mischaracterizations of the location of emission impingement on a substrate, sweep speed across the substrate, and resulting detected signal to take into account a number of possible characteristics which may influence the actual versus presumed location on the substrate which accounts for the signal collected. These may include or result in basic geometric nonlinearity resulting from beam altering effects which may be used to control beam direction, but there may not be a practical way to completely correct all sources of this, as well as any other elements that can distort the image. Other characteristics may contribute to image distortion resulting from signal measurement offset; these include errors introduced by scanning electronics, non-linear amplification, electric and electrostatic field variation, signal detectors (including electronics, lenses and other signal collection and detection means), non-linear or incorrect correction mechanisms and algorithms, and others. While the distortion contributed by each factor is complex in its own right, the combination of such factors, known and unknown, result in an associated distortion that was difficult to account for and whose impact was associated with very high resolution imaging; moreover, such distortion is not the same at all locations on a substrate or over time. With high resolution imaging these small un-corrected distortions can cause unwanted errors, and as the imaged features become smaller and smaller, the unwanted errors may cause more significant distortion in resulting images. The distortions at even a sub-pixel level may lead to unwanted errors. Methods, systems, and devices are required that provide a solution to this distortion resulting from numerous and complex sources.

Another associated issue relating to image distortion occurs when multiple images collected by scanning imaging devices are mosaicked together, or features on adjacent images are connected or linked in some way (e.g. a line of circuitry is followed across two or more images). Since the distortion is often consistent, it may have been possible to maintain integrity in such mosaics or connections provided that the entire imaged surface of a substrate was imaged using images of the same resolution and which represented the same dimensions of the substrate; this enabled the alignment of adjacent distorted images without losing too much integrity, since the relative distortion at the edge of images of similar resolution and substrate areas was also similar. Given, however, that some substrates have significantly different feature density and size in different areas, a mosaicked image must use constituent images with a resolution and size sufficient for the densest or smallest features on the substrate, even if portions of the substrate would not ordinarily require such images, thus greatly increasing the number of images required to create a mosaic of images of an entire layer in some cases. This problem may be further exacerbated when the images (or mosaics of images) of any given layer or cross-sectional representation of substrate are aligned with each other vertically, as may be required for example when carrying out assessment and/or reverse engineering of semiconductor devices, or 3-dimensional modeling of biological, geographical, and other 3-dimensional structures which are modeled using cross-sectional images. The resolution of the image and size of imaged area could be then associated with the smallest or densest feature found anywhere on any layer or cross-section. There is a need to correct distortion of images to enable correct alignment of images of different resolutions and/or capturing different sized areas of the imaged substrate.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein.

DETAILED DESCRIPTION

Figure 1:
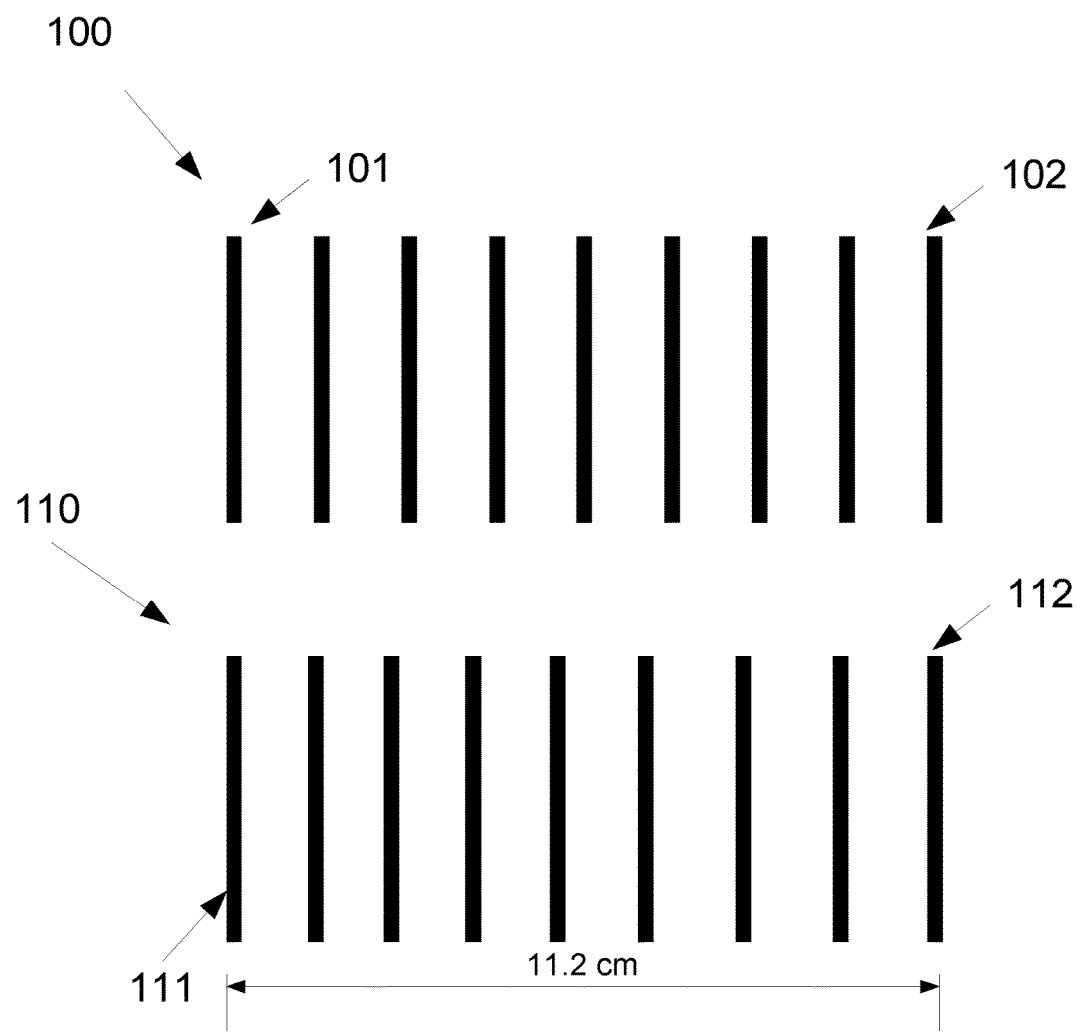
FIG. 1 is a diagrammatic representations of a portion of substrate and an image of the same substrate for illustrating the distortive effects of discrepancies between actual locations of image capture and intended locations of image capture.

The present invention will now be described more fully with reference to the accompanying schematic and graphical representations in which representative embodiments of the present invention are shown. The invention may however be embodied and applied and used in different forms and should not be construed as being limited to the exemplary embodiments set forth herein. Rather, these embodiments are provided so that this application will be understood in illustration and brief explanation in order to convey the true scope of the invention to those skilled in the art.

In general, imaging systems acquire image related data from at least one portion of a substrate and then translate that information, based on the location on or within the substrate that relates to the image data capture. For example, light, natural or from a source of illumination, is reflected from a surface and one or more light intensity measurement devices associate one or more light intensity values with the location from which the light reflected. Similarly, in ion beam or electron beam devices, a beam of particles is emitted towards a substrate, and the intensity of the reflected particles is indicative of features of the substrate; in such devices, the intensity data is associated with the region from which the particles are reflected. In transmission electron microscopy, an emission of particles (or light or other electromagnetic radiation) is directed through a material and the intensity of detected emission on the other side of the substrate is indicative of features of the substrate at the substrate location where the emission passes therethrough. In each such case, there is often a discrepancy between the intended location of image data capture, and the size of the region that is intended for image capture at such location, and the size and location of the true impingement of said emission on or through the substrate. When the values associated with the image data capture are assigned a location on a resulting image, the discrepancies between the intended location and size of the region of image capture and the actual location and size of the region of image capture will lead to a distortion of the resulting image from the collected image data. Embodiments hereof may characterize the discrepancy for various relative arrangements of the emission source, the emission, the substrate, and the emission detector; in some cases, the discrepancies may be characterized in association with one or more operating parameters of the imaging system. Embodiments hereof may correct the location and/or size of the region of image capture associated with each image data collection, based on a characterization of the discrepancies. Embodiments hereof may generate images, and portions thereof, by determining image pixel values based on the one or more image data collections that have a corrected location and/or size that correspond, at least in part, to the pixel location relative to the substrate.

There are numerous sources for the discrepancies between intended and actual image capture locations. For example, lens imperfections, irregularities in electromagnetic controllers, non-linear relationships between beam motivators and impingement points, imperfect correction algorithms and mechanisms, changes in environment, or any of a wide variety of complex or even unknown sources of error can introduce such a discrepancy. Many modern imaging systems attempt to account for these; as resolutions and magnifications increase, however, even the slightest discrepancy can result in distortion. In scanning devices, the discrepancies may further result in a nonlinearity between sampling rates and the rate of change of image capture location as the image capture mechanisms scan across the substrate.

It was observed, in some embodiments, that there is a strong relationship between the location of image data capture and the size and direction of the discrepancy; as such, for an otherwise constant set of operating characteristics, the nature of the discrepancy is generally the same at the same locations of image capture, irrespective of the substrate. For both scanning and non-scanning imaging devices, a correction factor that is related to the intended location of image data capture can thus be determined and then applied to locational data associated with any given image data.

When mosaicking, stitching, or otherwise aligning vertically or horizontally associated images, one past observation that has mitigated the issue relating to image distortion is that since the distortion is the same at the same locations for images at the same resolution, then images can be aligned to the extent that they are of equal size. For example, if adjacent images, either horizontally or vertically, are of equal size, the degree of distortion at corresponding vertices and edges will be the same. As such, a feature passing from a first image into a second image will align, and thus be imaged as being connected or forming parts of the same feature, if the adjacent images are the same size and aligned appropriately so that the distortion of said connecting features are the same at these locations. If the images are of different sizes, they may not necessarily align at corresponding locations; the connecting features in the adjacent images will not necessarily connect (even if they do on the substrate), resulting in an incorrect mosaicked image or aligned image. This results in a requirement for imaging all surfaces or cross sections of a substrate at the smallest resolution required in any location of the device. For substrates that are significantly larger in width and/or length than the corresponding dimension of an image, particularly if there are multiple layers that are to be aligned with one another, this may greatly increase the number of image captures that are required. In same cases, where the substrate may vary greatly in structure density, and the location and extent of such density is unknown prior to imaging, it may be necessary to collect image data far more extensively at every location and on every layer of a substrate. For example, when reverse engineering an integrated circuit, whose features are very small (<20 nm), of high and variable density, thus requiring very high resolution images, and which are connected across many different layers, imaging all portions for every successive layer is required at the same resolution that is required for the area having the smallest and/or densest features. This may, for example, result in capturing many thousands of images which are not required; thus consuming significant time and imaging and processing resources which could better be used elsewhere.

Any scanning imaging systems may be affected, including those that include (a) an incident beam that is scanned or swept across a sample resulting in an affected, emitted or reflected signal being detected; or (b) an affected, emitted or reflected signal that is detected by a detector that is scanned across a sample; or (c) a combination thereof. Imaging systems that do not scan a substrate, but rather capture one or more selections of image data at discrete locations on (or within a substrate) also exhibit discrepancies between intended and actual image capture locations and, as such, may have image distortion correction methodologies and systems as disclosed herein applied thereto. Non-scanning imaging systems may also be impacted. Any system which associates captured image related data with a location, and which may experience discrepancy between the intended location associated with the captured image related data and the actual location associated with the captured image related data, may have distortion caused by such discrepancy resolved or mitigated in accordance with the subject matter disclosed herein.

In many beam-oriented systems, the specific cause of distortion is unknown, as indeed is the existence and degree of any correction to the distortion that has been applied by the manufacturer. In scanning beam-oriented systems, there may be a sampling rate associated with image data collection that is associated with the rate of change of the location of beam impingement across the sample; while generally assumed to be linearly associated. This is in general an incorrect assumption, especially as resolutions increase. Discrepancies are therefore increasingly problematic to image integrity and the correction therefor increasingly ineffective. The final image may be distorted on a sub-pixel level; i.e. even within a pixel there is distortion.

In one exemplary embodiment of the instant subject matter, there is provided two imaging systems, the first comprising a first scanning electron microscope ("SEM1") and the other comprising a second scanning electron microscope ("SEM2"). Each system also comprises (or shares) a high resolution image-related data capture system, a computing processing device being communicatively coupled to the applicable SEM and the high resolution image-related data capture system and having loaded thereon software to (1) apply distortion correction to individual images in accordance with the methodologies disclosed herein; (2) provide "image stitching" for adjoining adjacent images; and (3) mosaic, overlay and navigate mosaicked images. Each system will operate in connection with a calibration sample consisting of a substrate with a series of grid lines with known dimensions with at least nanometer precision, and be used in imaging samples (e.g. an integrated circuit sample). In operation, the system determines the appropriate distortion correction by location for a given set of operating conditions, by taking a series of SEM images of the surface of the calibration sample at specified operating conditions on each SEM. The different operating conditions include the working distance (generally fixed at or around 8 mm), pixel dwell time (generally fixed at 0.20 microseconds per pixel), aperture size (generally fixed at 60 um), detector signal amplification range (generally fixed at "High"), image pixel resolution (generally fixed at 16000×16000), accelerating voltage (generally fixed at each of 8 kv, 9 kv, 10 kv), field of view or "FOV" (generally fixed at each of 50 um, 75 um, 100 um, 150 um). Using the calibration sample by comparing it with resulting images from the device, the correction values by substrate location, or distortion curve, representative for each permutation and combination of the above parameters for each SEM can be determined. Any number of parameters, not just limited to those listed above, can also be varied with data collected therefor over the sample to give a more fulsome distortion curve for a complete working range of parameters used in any given imaging device, including the systems described above. It should be noted that not all parameters influence the distortion to the same degree, and depending on the equipment being used, some simplification of parameters can be employed. A Design of Experiment method can be used to better characterize the effect of each parameter, including the interactions therebetween. Each specific SEM (even from the same vendor and operating at the same operating parameters) can have different sensitivities and distortions; only by measuring the full range of parameter space over the full FOV and for each image, and making a decision based on the final precision required, can the correct distortion values be employed. In the exemplary system above, single pixel accuracy is required, but sub-pixel or supra-pixel accuracy may be required in some cases.

Once correct distortion values have been established for a given system at specific operating conditions, an unknown sample (e.g. a partially delayered IC) may be imaged using the most appropriate parameters. In general, the most basic requirements require faster imaging (and thus a relatively larger FOV) while still having sufficient pixel resolution to identify the smallest circuit elements. If such elements are too small for useful imaging at the given pixel resolution, a smaller FOV with higher resolution may be required. While this may require the imaging to be repeated for that region of the substrate, this may provide the best way to determine general location of small/dense features and the necessary resolution associated therewith.

Figure 7:
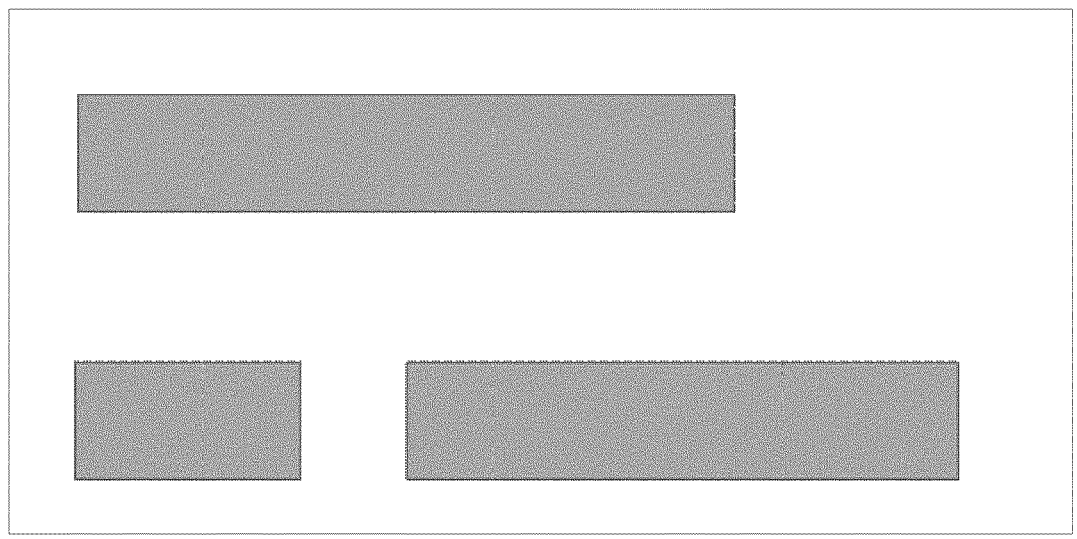
FIG. 7 is a representation of a magnified portion of an image from a mosaic of images taken of a first layer of a substrate in accordance with one embodiment of the subject matter disclosed herein.

With respect to the systems described above, the following initial settings may be used on SEM1: 1000×1000 um imaging area; a 100 um FOV (each image captures an area of 100×100 um); a mosaic of 10×10 images (100 images total; a 16,000×16,000 pixel image capture for each image (6.25 nm/pixel); an acceleration voltage of 10 kV; an image capture device with 60 um aperture; and "High" gain signal amplification. The location-based correction distortion values were applied to the images to create a new undistorted set of 16,000×16,000 pixel images, which can then be reliably aligned into a mosaic of images that provides an undistorted image of the applicable FOV of the imaged layer of the sample. FIG. 7 shows a magnified portion of one single image.

Figure 8:
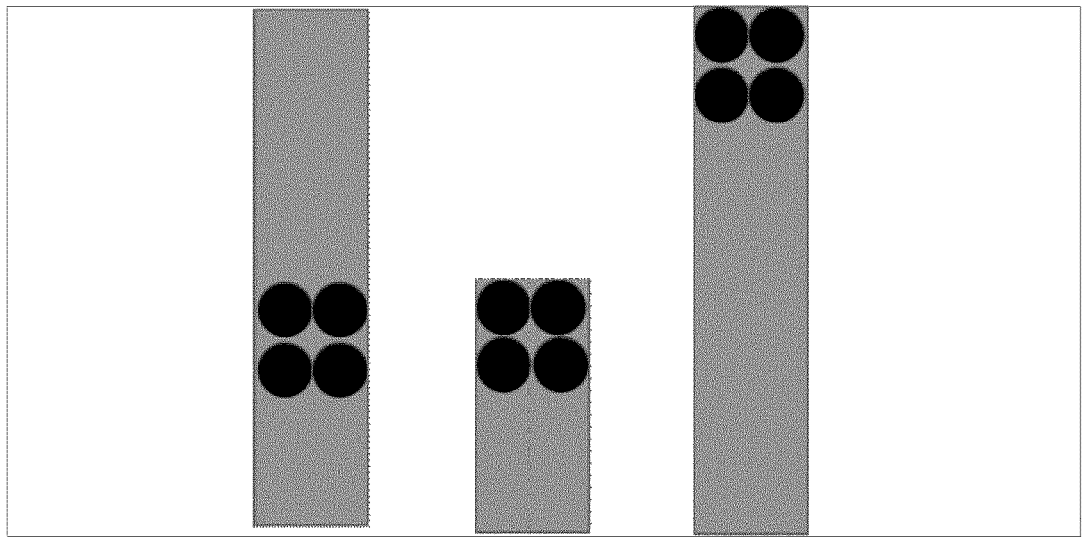
FIG. 8 is a representation of a magnified portion of an image from a mosaic of images taken of a second layer of a substrate, corresponding to the location of the magnified portion of an image shown in FIG. 7, in accordance with one embodiment of the subject matter disclosed herein.

The sample may then be partially delayered again to reveal the next layer of the sample (specifically, in the case of the IC example, additional circuitry) and the imaging step repeated but with slightly different parameters (to match the newly exposed circuitry layer with smaller circuit elements) on a different SEM. For example, SEM2, with 1000×1000 um imaging area, 50 um FOV (each image is 50×50 um), a mosaic of 20×20 images (400 images total), 16,000×16,000 pixel image capture (3.125 nm/pixel), an acceleration voltage of 8 kV, a 60 um aperture, with "high" gain signal amplification. FIG. 8 shows a magnified portion of one single image in a location that corresponds in both x and y coordinates to the image shown in FIG. 7.

Figure 9:
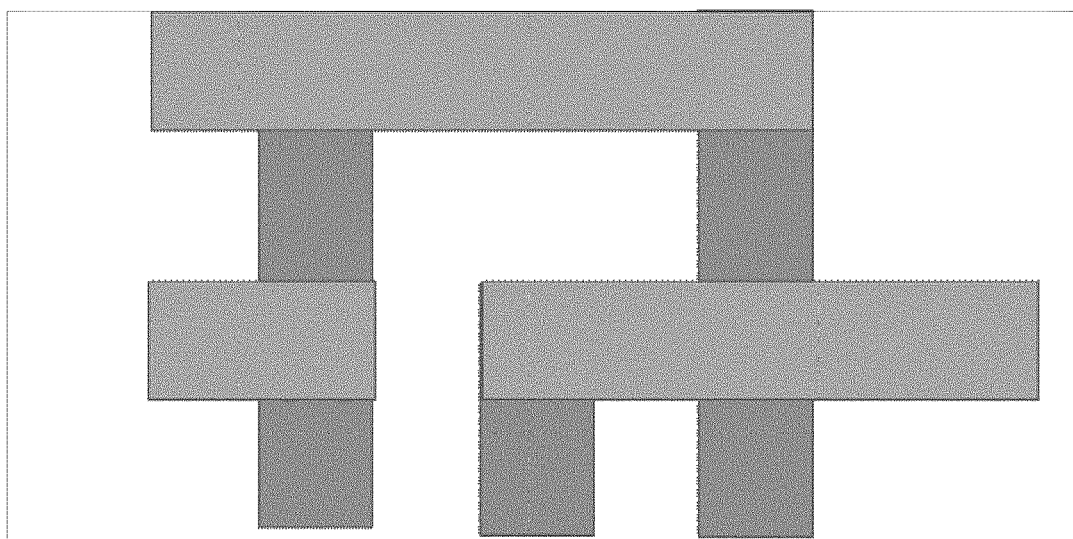
FIG. 9 is a representation of a distortion-corrected magnified portion of an image from a mosaic of images of a first layer overlaid with a distortion-corrected magnified portion of an image from a mosaic of images taken of a second layer, in accordance with one embodiment of the subject matter disclosed herein.
Figure 10:
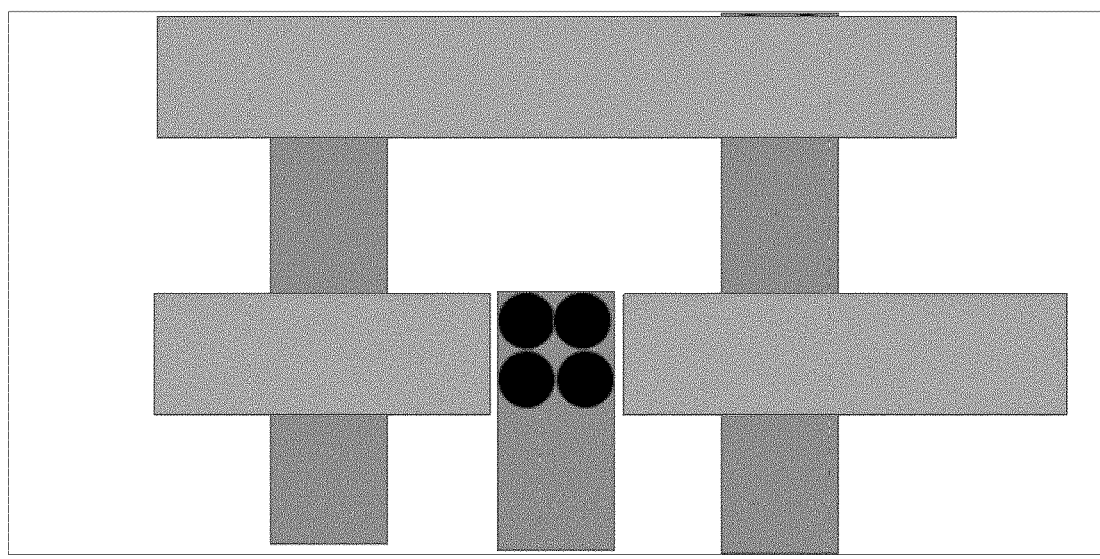
FIG. 10 is a representation of a non-distortion-corrected magnified portion of an image from a mosaic of images of a first layer overlaid with a non-distortion-corrected magnified portion of an image from a mosaic of images taken of a second layer, in accordance with one embodiment of the subject matter disclosed herein.

Location-based distortion correction values suitable for each SEM and each set of conditions were applied to each individual image from both data sets. After correction, the sets of images were stitched, aligned and arranged in a mosaic. One image set was overlaid on the other image set and showed perfect alignment for features of a few pixels in size. As shown in FIG. 9 (a magnified portion of one single image from the mosaic), the distortion-corrected images can be shown overlaid with one another, wherein the corresponding features on each layer align with one another, despite being taken by different SEMs, at different operating conditions and image resolutions. The result of stitching, aligning and overlaying uncorrected images, particularly in this case resulting from the different resolutions on different SEMs, may show significant instances of non-alignment between features from one data set to the other, as can be seen in FIG. 10 in which the same magnified portion of single images corresponding to those shown in FIG. 9 are shown overlaid without distortion correction.

In a typical image capture of a substrate surface, a beam, which could be optical, electron, ion, electromagnetic, etc. passes over an area whose image is being captured. In many cases, the substrate is scanned in a raster pattern in order to get more complete data collection from a surface or cross-section or portion thereof. A raster pattern is generally characterized by a first pass along a first direction from a first side to a second side, then a quick return back to the first side at a position just above or below in a second direction to the starting point of the first pass, and then a further pass along the first direction from the first side to the second side along a path that is parallel to the first pass, and then repeating. Not all raster scans are done in parallel lines; some are zigzag, star-shaped, serpentine, randomly oriented passes, or other shapes. Different portions of a substrate surface or cross-section need not be collected along a scanned path, with samples taken at one or more sampling rates; one or more discrete image capture locations may be collected by moving beam/substrate/collection device orientation to any given position, operating the beam emission and detection, collecting image related data, associating it with the intended location, and then determining a correction factor based on the intended location. The one or more discrete locations of image collection can be used to characterize the features or characteristics of the imaged surface, cross-section, or region thereof.

In some embodiments, an image of a portion of a substrate surface is captured when a beam is directed at the surface along the pattern described above while a suitable detector measures the emitted, reflected or affected signal. The measured signal can be collected (or recorded) at a predetermined sampling rate. In the case of an electron-based imaging system, electrons can reflect (backscatter), be absorbed, or trigger emission (secondary electrons or x-ray). Ion beam systems can, in addition to absorption and reflection, generate secondary electrons that can be used to characterize the image capture location. Light (e.g. laser and/or visible light) can reflect or generate photon emissions for substrate image capture characterization. Other beam-oriented signals may also be used. The resulting measurements (i.e. image-related data) are analyzed and used to generate an image based on the intensity of the measured signal, which will vary depending on the shape of and features on the surface, the composition and structures thereon that affect how many electrons are directed towards the detector, etc. In many electron imaging devices, the detector is configured to measure or record a sample at regular intervals as a beam motivator moves the location of beam impingement (by changing the direction of the beam or the relative position of two or more of the beam emitter, the substrate, and the emissions detector) at a desired pre-determined rate. Each sample corresponds to a pixel, group of pixels, a portion of a pixel (e.g. multiple samples can be combined to form a single pixel), or an image component.

The direction of sweep of the electron beam in electron imaging devices, and the rate of change thereof during a pass, is generally controlled by the generation and control of electromagnetic fields using one or more opposing pairs of electrodes having a potential difference therebetween. By manipulating the relative strength of the voltage at each electrode, the direction of the beam can be controlled. The voltage of each electrode is in many cases controlled by a digital-to-analog converter (i.e. DAC) and a respective voltage amplifier, which, although typically highly specialized and precise for generating very precise and accurate voltages, may produce a small number of unexpected fluctuation in the resulting electromagnetic field and thus some variations in the speed of the movement of the beam across the sample region being imaged and ultimately the location of the beam at any given time may not correspond to the expected location. For example, the rate of change of the image capture location may slightly speed up or slow down as the beam impingement location approaches the edge of the image capture area (relative to the rate of change nearer the centre of the image capture area). Moreover, as the lateral field of view increases the speed of the beam changes towards the edge of the sample (this may or may not be correct, the electronics might take this into account and the lensing also affects this). Due to the non-linear rate of change of the position of the beam, coupled with regular sampling intervals of the electron detector, the result is a distorted image since the electron imaging device identifies pixels in a given image from locations which may be closer together (or farther apart) in the middle of a given pass than the locations associated with adjacent pixels closer to the beginning or end of a pass. Moreover, this relative distance between adjacent pixels may be different for passes closer to the top or bottom than a pass through closer to the centre of the sample region. The area of impingement at a given location on the image capture region may change relative to other locations on the image capture region. In any case, distortion can also result from the impact and interaction of many components. Even if the beam is in fact swept at a linear rate, the optics and lenses of the system can influence the final location of the beam on the sample.

In many applications, the resulting distortion in any one application is not sufficiently significant to impact the ability to recognize adjacent features in any given image, nor align adjacent images. However, imaging a surface with high resolution on a surface (or cross-section) will exacerbate any distortion, no matter how minimal the distortion at lower resolution. Aligning adjacent images into a mosaic may become problematic when there are a very high number of images per surface (or cross section), particularly when the field of view for each image capture region is large and/or when the surface being imaged is very large relative to the image capture region size and/or the feature size and/or required resolution.

Distortion results in errors in aligning multiple mosaicked images vertically since structures that are used for vertical alignment from one layer to another may not align due to image distortion making it difficult if not impossible to identify the location of alignment; moreover, even if adjacent structures can be identified, the alignment in one region or location of two adjacent layers may cause misalignment with respect to one another. In the example of reverse engineering an IC, misalignment of a circuit lead will lead to misidentifying a disconnect in a given circuit. In some embodiments, different types of detection and imaging might be used, for example to assess various properties of a substrate, including density, materials analysis and/or chemical composition, and other properties or characteristics across a surface or cross section. For example, a system might use a secondary electron detector (SE) in one image, then a backscatter electron detector (BDS) in another image, then an energy dispersive x-ray spectroscopy (EDS) map in a third image, in some cases all with different field of view (magnification). By ensuring that any distortion is corrected, the various images of the same substrate can be overlaid without causing misalignment of features and structures.

This problem can be mitigated to a certain extent by minimizing the size of sample regions, and ensuring the same size and vertical alignment of sample regions of all imaged layers and then ensuring that all images have vertically-aligned vertices and/or edges with respect to one another. Provided they are aligned according to their vertices, a vertically oriented structure will appear in corresponding vertically-aligned images. Unfortunately, not all regions of any given layer and indeed all layers have equal or similar density of structures. In order to ensure that distortion of sample regions align across all overlaid images, however, to ensure that mosaicked layers can be properly aligned, minimally and equally sized sample regions, which are perfectly aligned with adjacent overlay layers must be captured across all layers and from layer to layer.

In the example of recreating a three-dimensional structure where an image is taken, the imaged portion of the sample is removed, and another image is taken and then aligned vertically with the first image, and these steps repeated. The distortion can cause significant misalignment between layers, even if properly aligned at one location (i.e. alignment may be correct at the centre of the image, but there may be misalignment at the edges). The following are three examples of imaging a layer, removing a layer and repeating to build mosaicked and aligned stacks of images to characterize a substrate. (1) FIB/SEM: an image or mosaic of images is taken with SEM, the FIB slices off a layer, then the SEM takes another mosaic image, then FIB slice, then SEM image. (2) Microtome/SEM: an image or mosaic of images is taken with SEM, the microtome slices off a layer, the SEM takes an image of the surface, and the steps are repeated. (3) Delayering Integrated Circuits: the SEM takes images, then by other methods, such as mechanical or chemical removal of a layer, a slice is removed from the IC, then another SEM image is taken, and the steps of delayering and SEM imaging are repeated. In these and other cases, each image of adjacent layers in the same sample can be aligned to analyze the structures that exist within a given sample. In some cases, the removal of a layer is not necessary as there are some imaging techniques which can provide image related data for a cross section of a substrate without physically removing any portion of the substrate above and below the cross-section being imaged. Non limiting examples of cross-section imaging include the following non-limiting examples: magnetic resonance imaging (MM), nuclear magnetic resonance imaging (NMRI), magnetic resonance tomography, computed tomography (including but not limited to X-ray CT, positron emission tomography and single-photon emission computed tomography), computed axial tomography (CAT scan), computer-aided/assisted tomography, ultrasonography, or ultrasound. The image distortion correction methodologies and systems can be implemented in any system that may include the foregoing types of cross-sectional imaging.

The instant invention corrects distortion within each sample region thus permitting greater ease of alignment of sample regions in any given layer, but also permits the use of varying sample region sizes within any given layer and from layer to layer. This greatly reduces the number of sample regions required for completely imaging all layers of a substrate. By correcting each image in the mosaic to be more representative of the actual surface, alignment of the images and/or image vertices is no longer required, and different magnification imaging can be used on different layers, or indeed different regions on a surface without impacting mosaicking. In some embodiments, this is done by amending the coordinates of sampling in the resulting image to correct for the nonlinearity introduced by the system by measuring the imaged features of a test sample and comparing them to the actual known location of those features, which may depend on the characteristics of the electron imaging device and various chamber conditions. Image data representative of a true location of a pixel in an image can thus be estimated for any sample by correcting the location association with captured image related data, and the location can be corrected thus eliminating or significantly reducing the distortion.

In a first embodiment, the subject matter relates to methods and systems for comparing the features on the resulting image relative to the actual known location of the features on the sample at given conditions, and then applying such comparison as a function of the intended location to the captured image related. In another embodiment, the subject matter relates to methods and systems for applying a predetermined image correction factor to each captured image related data, prior to applying said image related data to the pixels in an image corresponding to the corrected values, thus correcting for image distortion across a capture region of a substrate. In another embodiment, the subject matter relates to methods and systems for dynamically applying an appropriate predetermined image correction factor depending on the resolution of a given image capture region of a substrate and the desired location of image related data capture, which resolution may be varied depending on actual or presumed feature density, and aligning any distortion-corrected images corresponding to said image capture region with one or more distortion-corrected images corresponding to vertically or horizontally adjacent image capture regions.

With reference to FIG. 1, there is shown a first pattern 100 to be imaged by an imaging system, and the resulting image 110 of the pattern 100. The image 110 has uneven vertical line pitch due to system scan and sample time nonlinearity, resulting from imperfections associated with the scanning imaging system. The vertical line displacement is 0 on the beginning, as shown by features 111 and 101, and at the end of the image, as shown by features 102 and 112. That discrepancy between the actual location of the features, which is known from pattern 100, and the image features 110, can be used to determine a distortion curve that can be used to determine the distortion correction factor as a function of the desired location.

Figure 2:
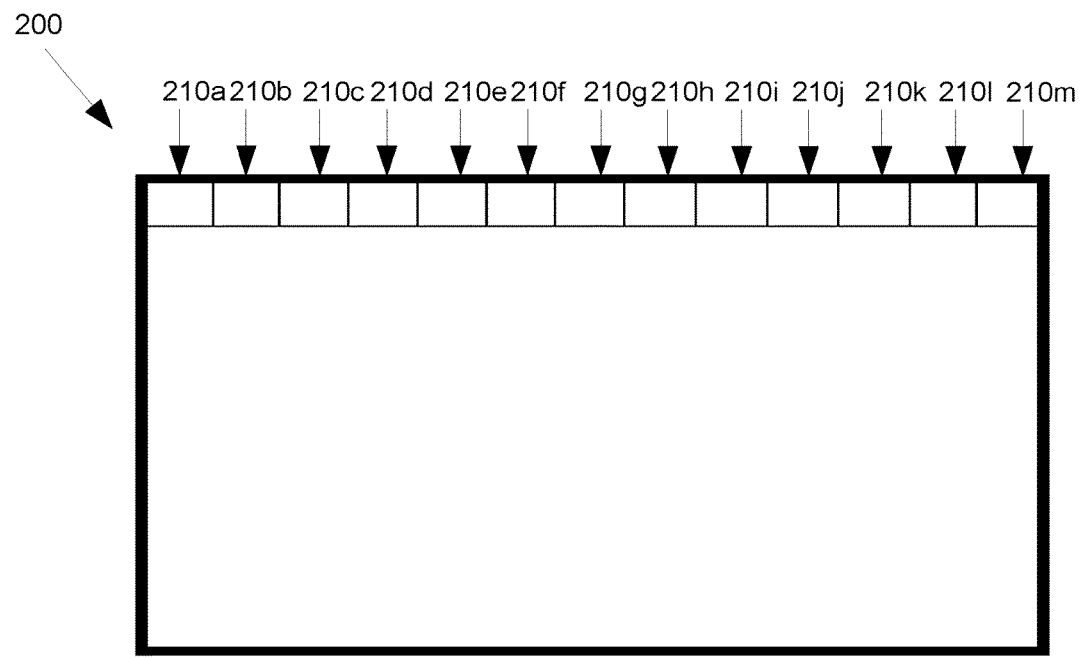
FIG. 2 is a representative diagram showing the first row of pixels for a given image generated in accordance with one embodiment of the instantly disclosed subject matter.
Figure 3:
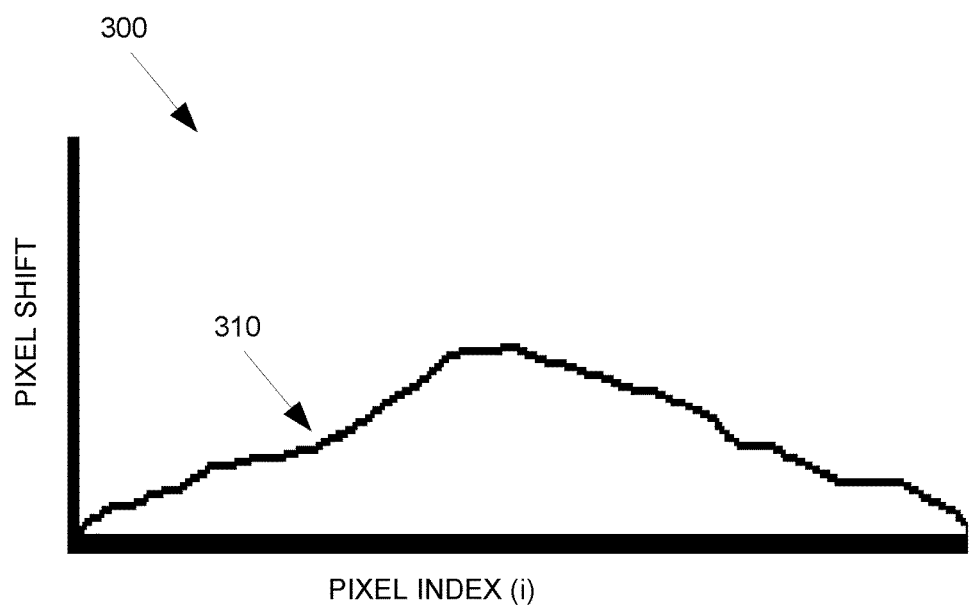
FIG. 3 is an exemplary and illustrative representation of a distortion curve for graphically representing location-based distortion of an imaging device in accordance with one embodiment of the instantly disclosed subject matter.
Figure 4:
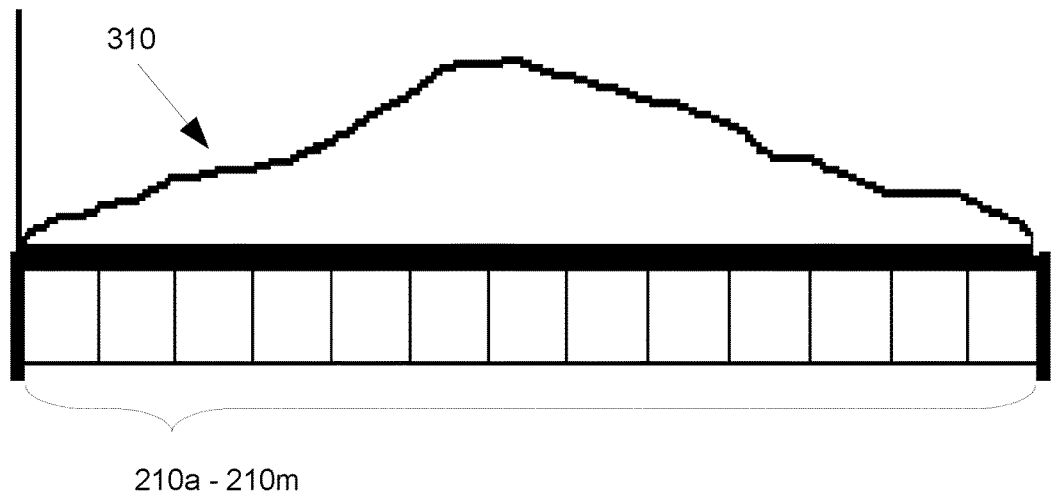
FIG. 4 is an exemplary and illustrative representation of a distortion curve for graphically representing location-based distortion of an imaging device, shown alongside a row of uncorrected image pixels in accordance with one embodiment of the instantly disclosed subject matter.
Figure 5:
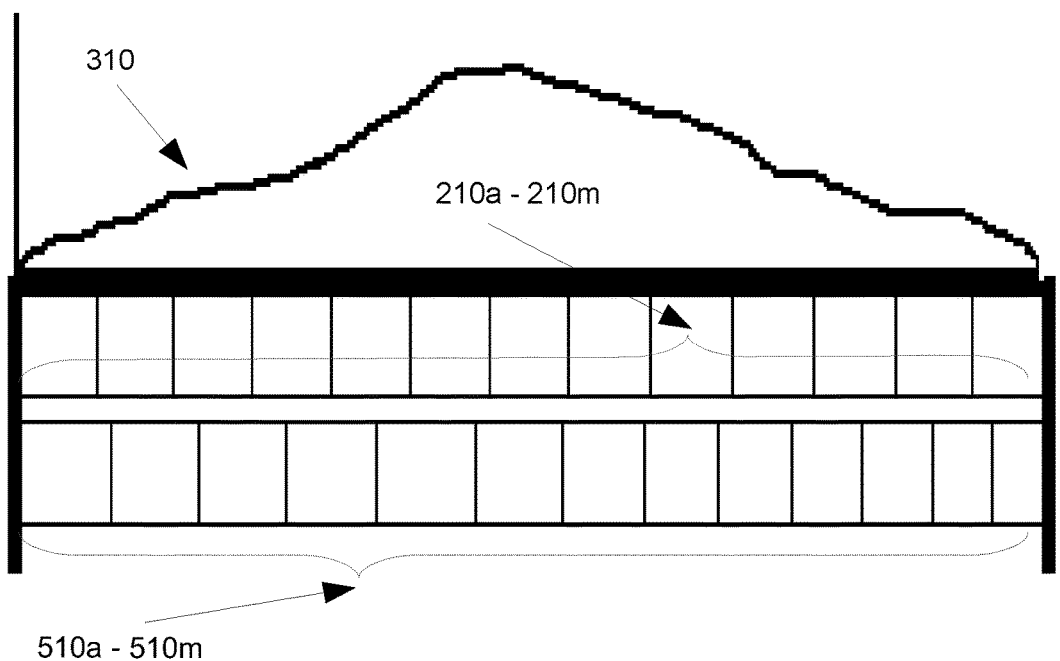
FIG. 5 is an exemplary and illustrative representation of a distortion curve for graphically representing location-based distortion of an imaging device, shown alongside a row of uncorrected image pixels and the location-corrected captured image data corresponding to said uncorrected image pixels in accordance with one embodiment of the instantly disclosed subject matter.

With reference to FIG. 2, there is shown the first row of pixels for a given image 200. In some scanning imaging systems, image related data is sampled at a given rate as the point of beam impingement is passed over the substrate; each sample is used to generate pixel values 210a to 210m. Due to non-linearities between the sampling rate and the scanning rate, distortion occurs. For the purposes of providing an illustrative example, it will be assumed that the same imaging system, operating at the same operational characteristics, generated the image 110 of the substrate with known features 100 shown in FIG. 1. By comparing the image 110 with the substrate with known features 100, a distortion curve can be generated. A distortion curve can be graphically generated that is representative of such comparison, as shown for example in FIG. 3. The distortion curve 310 in distortion graph 300 shows the degree of pixel shift that will be applied to the edge of each pixel in the row of pixels shown in FIG. 2, as shown in FIG. 4. FIG. 5 shows the result of such application, with the actual locations of data collection 510a to 510m shown. The location-corrected samples 510a to 510m represent the locations from which distortion-corrected image related data samples were collected. Since the pixel sizes are in fact fixed in the resulting image, however, the collected samples must be corrected to the fixed image pixels. This is accomplished by calculating a corrected pixel image value based on the samples of location-corrected collected image related values in proportion to the amount that each sample overlaps the fixed pixel. For a row of pixels, where only a single dimension is considered, the following exemplary equation is used to determine the corrected value of a pixel:

$$corrPx[i] = \sum_{j=1}^{n} px[j] * \frac{[j] \cdot \text{length}}{corr[i] \cdot \text{length}}$$

where i is the fixed pixel index in a row of pixels; corrPx[i]=is the corrected image related value for the $i^{th}$ fixed pixel in the row; j is the index of each location-corrected sample and portions thereof that overlaps the fixed pixel; n is the total number of location-corrected samples and portions thereof that overlap the $i^{th}$ fixed pixel; px[j] is the image related value collected for each location-corrected sample or portion thereof that overlaps the fixed pixel; [j].length is the length of each location-corrected sample or portion thereof that overlaps the fixed pixel; and corr[i].length is the length of the $i^{th}$ fixed pixel. As a clarifying example, if only a portion of a location-corrected sample overlaps a fixed pixel, the contribution therefrom to the corrected image related value would be the sampled image related value multiplied by the fraction of only the overlapping portion of the location-corrected sample over the fixed pixel length (and not the entire length of the location-corrected sample).

While FIGS. 1 through 5 exemplify embodiments associated with a row of pixels, or a distortion-correction across one dimension, such as the width of an imaged region, the same principles can be applied across two-dimensions and three-dimensions. A distortion curve can be generated to correct distortion across the length and width of an image region to compensate for discrepancies between intended and actual locations of sampling at all regions on a sample. For some applications and systems, at particular resolutions, distortion correction across width only may provide sufficient correction. In others, distortion correction across length and width may be required. The above formula would be amended to the following 2-D formula:

$$corrPx[i] = \sum_{j=1}^{n} px[j] * \frac{[j] \cdot \text{area}}{corr[i] \cdot \text{area}}$$

where the values are the same as above. j remains the index of each location-corrected sample and portions thereof that overlap the fixed pixel, except in this case, the proportion of each image related value used in the corrected image related value is based on the overlapping area of each location-corrected sample or portions thereof. For three-dimensions, a different two-dimensional distortion curve may be generated for each cross-section of a substrate or a full three-dimensional representation of the distortion curve can be generated across an entire volume of a substrate. In the case of the former, the 2-D formula may be applied to every layer using a 3421 different 2-D distortion curve for each layer. Alternatively, a full 3-D distortion curve can be generated, in which the above formulas would be calculated on the basis of the proportion of the volume of each location-corrected sample, or portion thereof, within the fixed 3-D pixel, to the volume of the fixed 3-D pixel. The 3-D distortion curve and applicable distortion-correction would be used for cross-sectional analysis when layer removal is not possible or desirable, and the imaging method does not require such removal.

In one embodiment, there is provided an imaging device for imaging a substrate, the device comprising a beam emitter for directing an emission at an intended location on the substrate so to produce a detectable signal representative of the substrate. The beam emitter may be an integral component to the device that both generates and directs a beam of a specified beam composition, with definable operating characteristics (e.g. composition, intensity, etc.). In other cases, the beam emitter may allow or direct ambient light or other electromagnetic radiation towards the substrate. The beam may comprise the following non-limiting examples: light, electrons, ions, x-rays, magnetic energy, electromagnetic energy. In other words, the imaging system may be an optical imaging system, or it may impinge the sample with different types of particles (e.g. electrons, ions, etc.), or it may impinge the sample with various forms of electromagnetic radiation or energy (e.g. x-rays, magnetic waves, etc.). The emissions from the beam emitter cause a detectable signal to be generated by the substrate, the signal being associated with a specific location thereon. The detectable signal may include the scattered or reflected beam that was emitted, or it may comprise secondary electrons or other excitations. Either way, the impingement of the emission results in a detectable signal from a specific location on or in the substrate.

In some embodiments, the intended location on the substrate is on an exterior surface of a substrate. The detectable signal may be collected or measured in respect of a plurality of intended locations on the substrate in order to characterize a surface of a substrate for the purposes of generating an image. In some embodiments, the intended location is on an interior cross-section of a substrate; in such cases, the detectable signal may be collected at locations along a cross-section of a material, or along interior features. In some cases, multiple cross-sections are imaged and aligned in order to develop a 3-D model of the substrate. Alternatively, a 3-D model, or images can be aligned vertically, by imaging a surface of a substrate, removing a layer from the surface, imaging the exposed surface, and repeating; the resulting images can then be aligned vertically. The latter method results in repeated de-layering and thus, in most cases, destruction of the substrate.

The device further comprises a signal detector for detecting an imaging characteristic of said detectable signal. In the following examples, a detected imaging characteristic of the detectable signal is generally associated with a detected intensity of this signal. The skilled artisan will however appreciate that different signal characteristics may be measured and/or quantified, alone or in combination, to image a particular substrate, such as a signal wavelength, colour, frequency, phase, spectrum, intensity or the like, and that, without departing from the general scope and nature of the present disclosure.

In some examples, the detectable signal may be a reflection or back scatter of the emission output from the beam emitter (e.g. electrons in scanning electron microscope (a "SEM"), ions in a focused ion beam device (a "FIB"), or light in an optical system). In other cases, the detectable signal is the emission that passes through a sample (e.g. TEM). In other cases, secondary particles, such as electrons or ionized particles may be generated upon impingement of the emission, and the signal detector may measure or detect an intensity associated therewith. In other cases, the emission may cause other types of excitation (and resulting relaxation) which is detected by a signal detector and associated with an intended location.

The imaging device is configured to automatically associate said intensity with a corrected substrate location for use in generating a distortion-corrected image, wherein said corrected substrate location is determined from said intended location and a correction factor that is a function of said intended location. For any given system, the correction factor is pre-determined based on the intended location when at least one operational characteristic is maintained at a constant value. For example, while chamber pressure, temperature and ambient gases are maintained constant, and the beam intensity and composition is maintained at a constant level, the beam is passed over or directed at a substrate with known surface features. The resulting image is compared to the known surface features to generate a correction factor for each sampling location. While most systems attempt to minimize any error between the intended location of sampling, and the actual location (where location includes the size of the sample region), and indeed many systems also attempt to compensate for any such error, the instantly disclosed subject matter uses empirical data for the imaging system operating with at least one constant operating characteristic to produce the correct factor at every intended location on the substrate as a function of such location. As such, all sources of error, the complexity and interaction therebetween, and compensations therefor becomes immaterial since every system at a given operating state can be characterized, and such characterization can be applied to all future uses at such operating state to correct distortion. The correction factor can then be applied to determine the actual size and location to which the detected signal relates, and the resulting image can then be corrected for any distortion, no matter how complex the causes of the distortion.

In some embodiments, the system is a scanning imaging system that uses one or a combination of a beam emitter motivator, a substrate motivator, or a signal detector motivator to measure signal intensities associated with different intended locations on the substrate. In some embodiments, such as those using a SEM and/or a FIB, electromagnetic coils are used to alter the shape and/direction of the beamed emission by changing the potential drop around such coils to sweep the beam over the substrate. In some embodiments a mechanical motivator may change the orientation and position of the beam emitter itself. In both such cases, the substrate and the signal detector remain stationary. In other cases, the emitted beam is maintained in the same orientation and direction, while either or both of the substrate and/or the signal detector is moved. In some cases, a combination of these components can be moved or remain constant. In any case, a signal associated with a specific location on the substrate should be associated with a given signal intensity measurement. For a scanning imaging device, the beam passes over the substrate in a predetermined path and samples are measured at a pre-determined rate. For other types of devices, the rate of sampling need not be germane since the device may collect samples at pre-determined intended locations and then use the intensity levels and intended locations (corrected for distortion) in generated image data.

Figure 6:
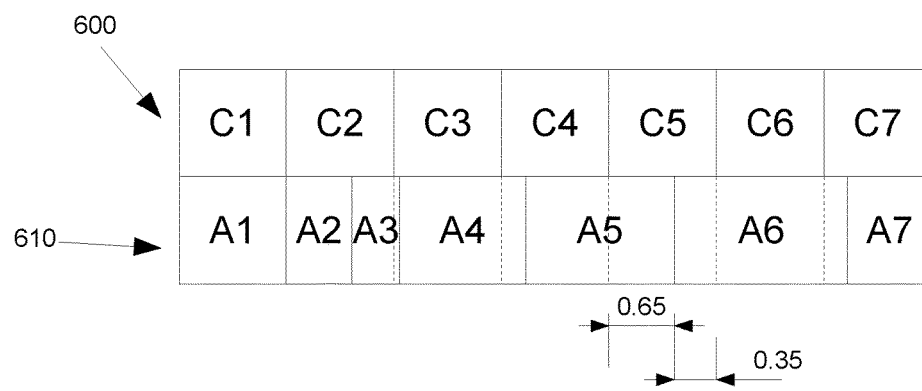
FIG. 6 is a diagrammatic representation illustrative of image pixel locations alongside corresponding location-corrected captured image related data in accordance with one embodiment of the subject matter disclosed herein.

In some embodiments, a plurality of samples of signal intensity values, each associated with an actual location on or in the substrate, are used to generate image pixels. Since the actual locations of the substrate will not necessarily align with the pixels of the image, they should be corrected. In some embodiments, this is accomplished by associating each pixel with a corrected intensity value, said pixel using said corrected intensity value to populate the pixel with a pixel image value, which may in turn be used to determine a colour or grayscale value for said pixel. There is an image pixel value and an image pixel corresponding to each intended substrate location, and the image pixel value is based on respective proportions of the at least one signal intensity value whose corrected substrate location corresponds to a portion of the image pixel. The corrected intensity value for each pixel image value is determined using a proportion of each intensity value that is associated with a corrected location corresponding to that pixel location, said proportion being equal to the proportion of the size of the corrected location to the pixel size. For example, if a pixel location corresponds to the same location as a given corrected location (or indeed if the corrected location is greater than the pixel), the corrected intensity value of the pixel is the same as the intensity measure from that corrected location. Referring to FIG. 6, an exemplary determination is shown. The intensity of C1, otherwise referred to as p[C1], in the row corresponding to the fixed image pixels 600 is equal to the proportion of all samples 610 with corrected locations corresponding to C1. In this case, C1 corresponds precisely to A1 and so p[C1]=p[A1]. Only A6 contributes to C6, so p[C6]=p[A6]. C5 corresponds to portions of A5 and A6; respectively, 65% of C5 is from a portion of A5 and 35% is from a portion of A6, so p[C5]=0.65p[A5]+0.35p[A6]. While other formulas and methodologies of determining pixel image values may be used in other embodiments, in general the contribution will be related to the detected intensity values associated with the actual locations detection that coincide with some or all of the pixel image value corresponding to the same location on the substrate.

In some embodiments, the device comprises the beam emitter, the substrate stage and the signal detector in an integral manner. In other cases, the device comprises a system in which each of said components is maintained in a non-integral portion. The association, measurement, determination, and correction steps may be accomplished by a communicatively coupled computing device, which may be integrally associated with the device or alternatively as a system that is non-integral to the device or system. Said computing device may comprise various combinations of processing, communicative, and data storage, and memory components, as will be appreciated by the skilled artisan.

In some embodiments, there is provided a method of correcting image distortion in an imaging device or imaging system. The imaging device or system comprises a beam emitter for directing an emission at a substrate so to produce a detectable signal representative of the substrate associated at an intended location, and a signal detector for determining an intensity value of said detectable signal. The method comprises the steps of: causing the emission to impinge the substrate so as to produce the detectable signal that is associated with an intended location, the intended location typically corresponding to the pixel location on the image of the region on the substrate being imaged. The detectable signal may be reflected, scattered or non-absorbed portions of the emissions from the beam emitter, or it may be a secondary signal caused by the impingement of the emission. An intensity of the detectable signal is measured by the signal detector is measured, said intensity being initially associated with the intended location of measurement; and a corrected substrate location is associated with the measured intensity, said intensity with associated corrected substrate location for use in generating a distortion-corrected image, wherein the corrected substrate location is calculated from the intended location and a correction factor that is a function of said intended substrate location. Once sufficient intensity values are measured from a portion of the substrate to provide image data for a region of the substrate (on a surface or a cross-section thereof), corrected intensity values are determined for each image pixel by associating proportionate quantities of all the corrected substrate locations that correspond to the pixel location at the imaged region.

In some embodiments, there is provided a method of determining the correction factor for a given imaging system at one or more constant operating characteristics. The method involves imaging, or detecting signal intensities associated with surface features on, a substrate with known surface features and then comparing the resulting image (or, as the case may be, signal intensity values associated with intended locations of measurement) with the known surface features. Based on the differences, a translation in one or more direction (or dimension, i.e. length, width, or depth) can be determined as a function of the intended location. The correction factor, expressed as a translation with direction, or a vector, at each intended location in a given substrate, may be expressed as one or more distortion curves or distortion indices. The correction factor can then be used for resolving distortion correction for any substrate imaged in the same device at the same operating conditions.

An exemplary set of imaging results from one embodiment is described, including, as shown in FIGS. 11 to 16, the resulting distortion-corrected images and the corresponding non-corrected images of the same substrate. This embodiment of a distortion-correction imaging system comprises a first scanning electron microscope (SEM-A), a second scanning electron microscope (SEM-B), a high resolution image capture system, a calibration sample (a substrate comprising a series of known grid lines with nanometre precision, the features of which are detectable by said capture system), an integrated circuit sample, an associated data processing device (e.g. computer) running various software applications, including software to apply the distortion correction process to individual images, image stitching software, mosaic overlay and navigation software.

An exemplary embodiment of one method of correcting image distortion in the above system, includes the following steps. Using both SEM-A and SEM-B, a series of SEM images are taken of the calibration sample at different operating conditions. Exemplary operating conditions may possibly include: a fixed working distance (8 mm), fixed pixel dwell time (0.20 microseconds per pixel), fixed aperture (60 um), fixed detector signal amplification range (High), fixed pixel resolution (16000×16000), accelerating voltages (8 kv, 9 kv, 10 kv), Field of View FOV (50 um, 75 um, 100 um, 150 um). By comparing the resulting image for each permutation and combination of the above parameters with the known features of the calibration sample, a relationship for each set of operating conditions can be determined as a function of the intended location (where the intended location may include the size as well as the location of the resulting capture location, since the size of the area upon which the beam is incident on the surface of the substrate may be different at different intended locations). A correction function may be developed, wherein the size and location of the actual area and location of image capture is returned for a given input of an intended location when capturing image data at a given set of operational parameters for the imaging device.

Ultimately, many parameters can be varied and data collected to give a complete working range for characterizing distortion at any given location within the FOV. It should be noted that not all parameters influence the distortion to the same degree, and depending on the equipment being used, some simplification of parameters can be employed. A Design of Experiment method can be used to reduce the number of tests. Each specific SEM (even from the same vendor) can have different sensitivities and only by measuring the range of parameter space and making a decision based on the final precision required can the correct algorithm be employed. In the present embodiment, single pixel accuracy was required.

Once the correction function is established, an unknown sample (partially delayered IC) is imaged using the most appropriate parameters (such parameter values shown in the table below) to give Image Set #1. The most basic requirements were fastest imaging (largest FOV) while still having sufficient pixel resolution to identify the smallest circuit elements. The following table shows the imaging parameters for each Image Set.

| Parameter | Parameter Value for Images Set #1 | Parameter Value for Image Set #2 |
|---|---|---|
| SEM | SEM-A | SEM-B |
| Imaging Area | 1200 × 1600 um | 1200 × 1650 um |
| FOV | 100 um | 75 um |
| Image Mosaic | 12 × 16 images | 16 × 22 images |
| Number of Images | 192 | 352 |
| Pixels per image | 16,000 × 16,000 | 16,000 × 16,000 |
| SEM kV | 10 kV | 8 kV |
| SEM Aperture | 60 um | 60 um |
| SEM Detector Gain | High | High |

Figure 11:
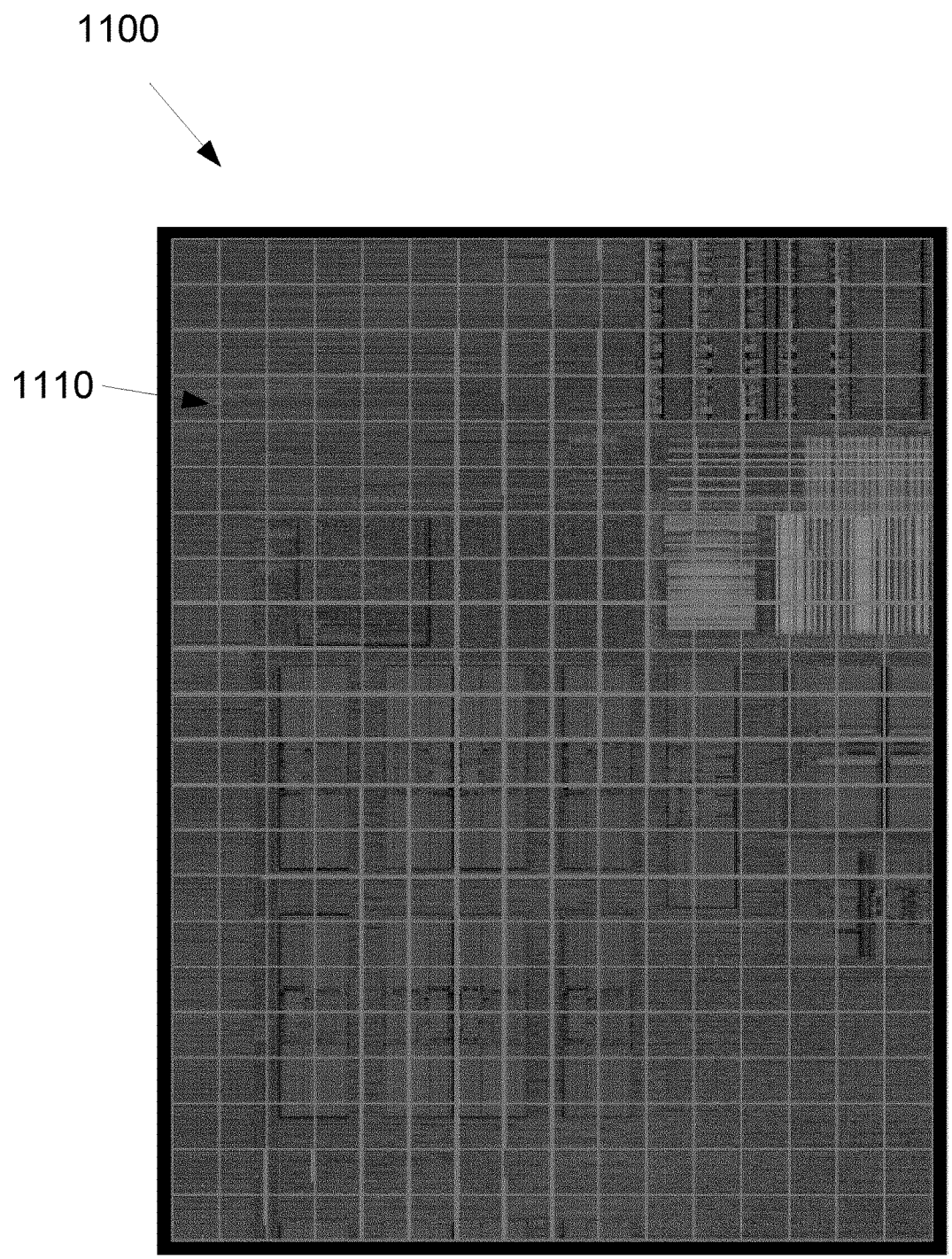
FIG. 11 is an exemplary image of an image set mosaicked together to show a layer of a partially delayered unknown sample in accordance with one embodiment of the subject matter disclosed herein.
Figure 12:
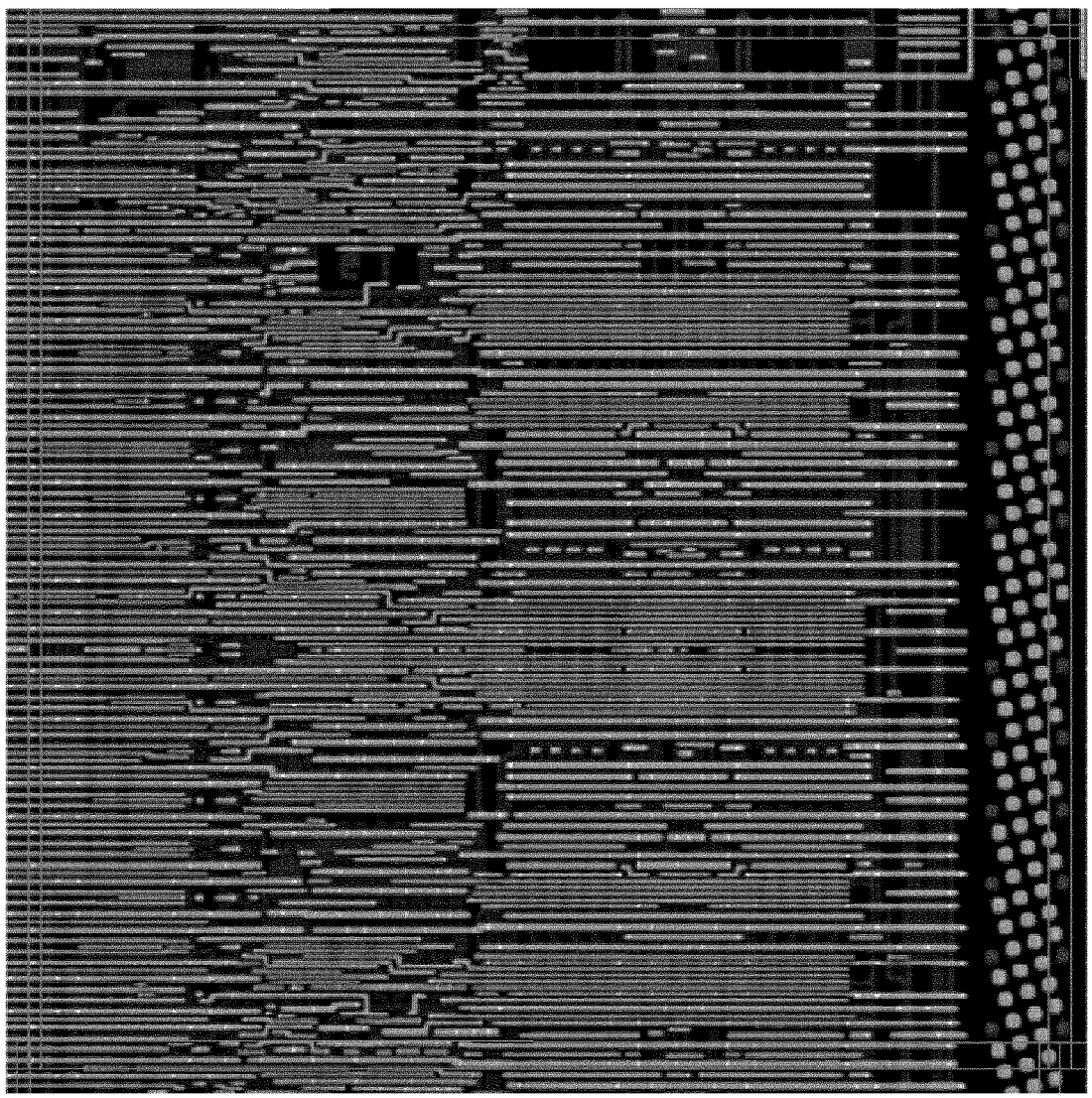
FIG. 12 is an exemplary image taken from the mosaicked image set shown in FIG. 11 in accordance with one embodiment of the subject matter disclosed herein.

After images were collected for the entire layer, the partially delayered IC was further partially delayered to reveal the next layer of circuitry and the imaging step repeated but with slightly different parameters (to match the newly exposed circuitry layer with smaller circuit elements) and using a different SEM. This created Image Set #2, which are mosaiced together to form an image of the entire imaged layer 1100, as shown in FIG. 11. The lines of alignment for each mosaiced image, e.g. 1110, are shown in FIG. 11. One individual image from Image Set #2 is shown in FIG. 12.

Figure 13A:
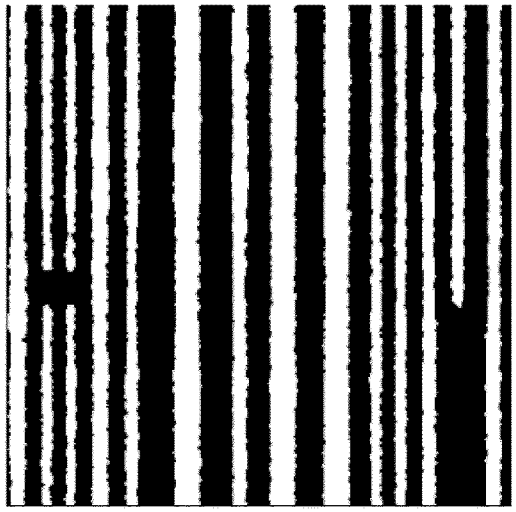
FIGS. 13a and 13b show magnified areas of images from a first set of images taken of a given layer of an unknown sample, respectively, near the edge of the imaged area and near the middle of said imaged area.
Figure 13B:
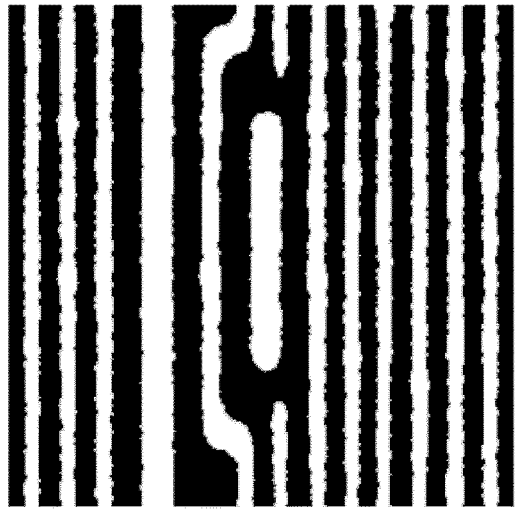
Figure 14A:
FIGS. 14a and 14b show magnified areas of images from a second set of images taken of a further layer of an unknown sample that is vertically adjacent to said given layer, respectively, near the edge of the imaged area and near the middle of said imaged area.
Figure 14B:
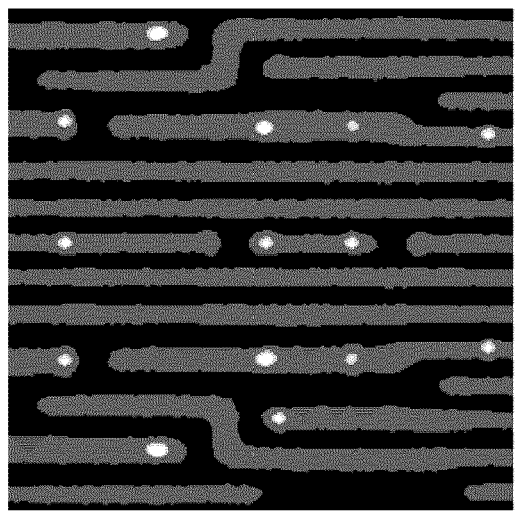
Figure 15A:
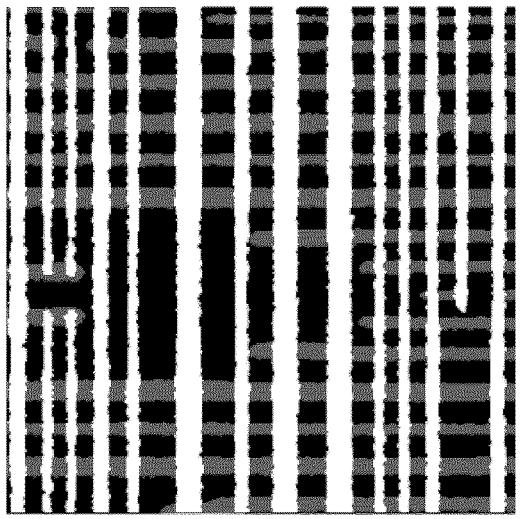
FIGS. 15a and 15b show overlaid images of corresponding areas of said given and further layers with image distortion correction applied, said areas being, respectively, near the edge of the imaged area and near the middle of said imaged area.
Figure 15B:
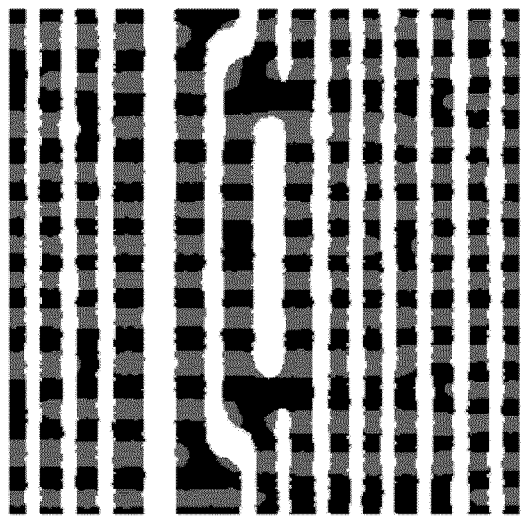
Figure 16A:
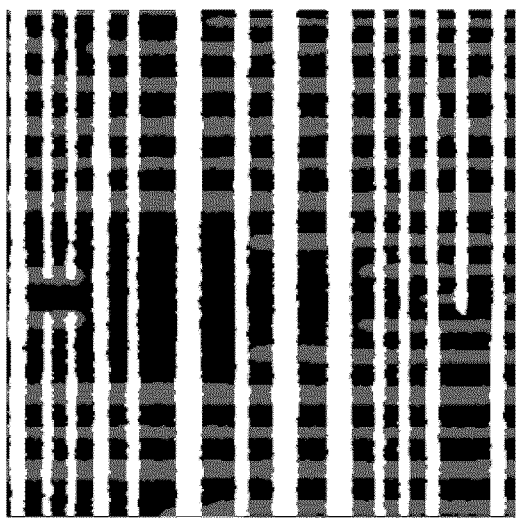
FIGS. 16a and 16b show overlaid images of corresponding areas of said given and further layers with no image distortion correction applied, said areas being, respectively, near the edge of the imaged area and near the middle of said imaged area.
Figure 16B:
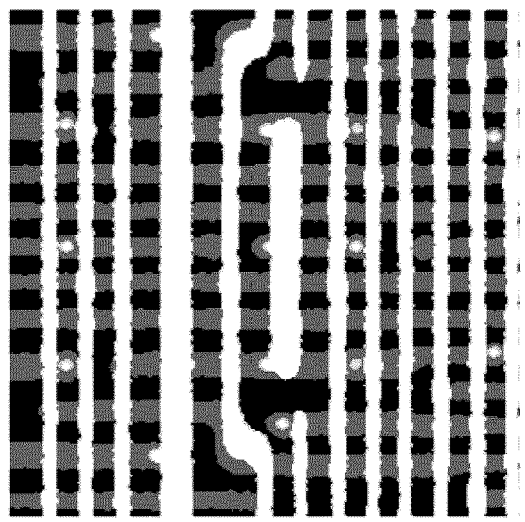

The distortion correction algorithm suitable for each SEM and each set of parameter values was applied to each individual image from both data sets. After correction, the sets of images were stitched, aligned and arranged in a mosaic. FIG. 13 shows two magnified areas from one image in Image Set #1. FIG. 13a is taken from near the left edge of an image, FIG. 13b is taken from near the centre. FIGS. 14a and 14b show two magnified areas from one image in Image Set #2; FIG. 14a showing an image from near the edge of Image Set #2 and FIG. 14b showing an image from near the centre of the Image Set #2. In FIGS. 15a and 15b, two magnified areas from one image in the corrected Image Set #1 is shown on top of corresponding magnified areas from an image in the corrected Image Set #2. FIGS. 15a and 15b show perfect vertical alignment, where interconnect vias from Image Set #2 line up precisely with metal lines in Image Set #1. This is true near the edge of the image and near the centre. In contrast, FIGS. 16a and 16b show the same areas but with the images not corrected. While the magnified areas are aligned well at the edge of the image, misalignment near the centre of the image is apparent.

While the present disclosure describes various exemplary embodiments, the disclosure is not so limited. To the contrary, the disclosure is intended to cover various modifications and equivalent arrangements included within the general scope of the present disclosure.

What is claimed is:

1. An imaging device for imaging at least a portion of at least one layer of a substrate, the device comprising:
   a beam emitter for directing an emission at the substrate so as to produce a detectable signal representative of the substrate at a plurality of intended substrate locations on the portion of the substrate; and
   a signal detector for detecting an imaging characteristic of said detectable signal for each of the intended locations;
   one or more motivators for changing a direction of said emission relative to a position of the substrate to detect said imaging characteristic at each of the plurality of intended substrate locations on the portion of the substrate;
   wherein the imaging device, for each intended location, automatically associates said imaging characteristic therefor with a corrected substrate location for use in generating a plurality of distortion-corrected images each with a given image resolution, wherein said corrected substrate location is determined from said intended location and a correction factor that is a function of said intended location and said given image resolution corresponding to said given intended location; and
   wherein the imaging device is configured to align the plurality of distortion-corrected images to form a mosaiced image of the portion of at least one layer of the substrate, said distortion-corrected images comprises at least two different image resolutions.

2. The device of claim 1, wherein said imaging characteristic comprises an intensity of said detectable signal.

3. The device of claim 1, wherein said correction factor is predetermined for at least one operating characteristic of said imaging device.

4. The device of claim 3, wherein said at least one operating characteristic comprises a current imaging resolution of the device.

5. The device of claim 1, wherein each of the one or more motivators comprises a beam motivator for changing a direction of said emission relative to a position of the substrate to detect said imaging characteristic at one or more different intended substrate locations.

6. The device of claim 1, wherein each of the one or more motivators comprises a detector motivator for changing a relative position of said signal detector to the substrate to detect said imaging characteristic for one or more different intended substrate locations.

7. The device of claim 6, wherein each of the one or more motivators comprises a stage motivator for changing a position of a stage holding the substrate relative to the beam emitter and the signal detector.

8. The device of claim 1, wherein said signal detector determines a corresponding characteristic for each of a plurality of different corresponding intended substrate locations, and wherein the imaging device automatically associates each said corresponding characteristic with a corresponding corrected substrate location for use in generating said distortion-corrected image, wherein each said corresponding corrected substrate location is determined from each of said corresponding intended locations and said correction factor that is a function of said corresponding intended locations.

9. The device of claim 1, wherein a given image pixel value for a given image pixel location corresponding to a given intended substrate location is based on respective proportions of said imaging characteristic associated with any one or more said corrected substrate location overlapping at least a portion of said given image pixel location.

10. The device of claim 1, wherein the device is selected from the following group: an optical imaging device, a FIB, a SEM, a TEM, an X-Ray device, an MRI, an ion beam device, a CT scan, and a CAT scan.

11. The device of claim 1, wherein mosaiced images of portions of at least two layers of a substrate are formed, and the device is further configured to vertically align corresponding locations of said portions sharing common features that pass through all such at least two layers.

12. A method of correcting image distortion in an imaging device, the imaging device comprising a beam emitter for directing an emission at a substrate so as to produce a detectable signal representative of the substrate at an intended location and location-dependent beam resolution, and a signal detector for determining an imaging characteristic value representative of the detectable signal, the method comprising:
  causing the emission to impinge the substrate;
  measuring the imaging characteristic of the detectable signal associated with the intended location and location-dependent image resolution;
  determining a corrected substrate location associated with the imaging characteristic for use in generating a plurality of distortion-corrected images, the corrected substrate location determined from the intended location and a designated correction factor predetermined as a function of said intended substrate location, each of said distortion-corrected image with an image resolution associated with the corresponding location-dependent beam resolution;
  associating said measured imaging characteristic of the detectable signal with said corrected location;
  repeating said measuring, determining and associating for at least one other intended substrate location; and
  aligning the plurality of distortion-corrected images to form a mosaiced image of the portion of at least one layer of the substrate, said distortion-corrected images comprising at least two different image resolutions.

13. The method of claim 12, wherein said imaging characteristic comprises an intensity of said detectable signal.

14. The method of claim 12, wherein said correction factor is further predetermined for a given set of operating characteristics of said imaging device.

15. The method of claim 12, further comprising associating a given image pixel value with a given image pixel location corresponding to the intended location on the substrate, said given image pixel value being based on respective proportions of said imaging characteristic associated with any one or more said corrected substrate location overlapping at least a portion of said given image pixel location.

16. The method of claim 12, wherein the method further comprises:
  mosaicing images of portions of at least two layers of the substrate; and
  vertically aligning corresponding locations of said portions on the at least two layers sharing common features that pass through all such at least two layers.

17. The method of claim 16, wherein the method further comprises:
  repeating said collecting, generating image pixel values, and generating images for each of at least two layers of the substrate; and
  vertically aligning corresponding locations of said images on the at least two layers sharing common features that pass through all such at least two layers.

18. A method of generating an image of a substrate from an imaging device, the imaging device comprising a beam source for directing an emission with a respective location-dependent beam resolution at an intended location on a substrate and a signal detector for determining a signal characteristic value associated with the emission, the method comprising:
  collecting a plurality of signal characteristic values by the signal detector, each of said signal characteristic values indicative of a substrate characteristic at an actual location;
  determining, for each given signal characteristic value, said actual location associated therewith by correcting said intended substrate location using a correction factor, said correction factor being a function of said intended substrate location; and
  generating image pixel values for the image, wherein a given image pixel value at a given image pixel location is based on: the respective location-dependent beam resolution for the given image pixel location, and respective proportions of at least one said given signal characteristic value whose corrected substrate location corresponds to a portion of said given image pixel location; and
  generating an image from a plurality of said image pixel values, said image pixel values comprising at least two different location-dependent beam resolutions.

19. The method of claim 18, wherein the correction factor is associated with at least one operating characteristic of the imaging device.

* * * * *